United States Patent [19]

König et al.

[11] 4,386,033

[45] May 31, 1983

[54] PROCESS FOR THE CONTINUOUS THERMAL CLEAVAGE OF CARBAMIC ACID ESTERS AND PREPARATION OF ISOCYANATES FROM THE PRODUCTS THEREOF

[75] Inventors: Klaus König, Leverkusen; Peter Heitkämper, Dormagen, both of Fed. Rep. of Germany

[73] Assignee: Bayer Aktiengesellschaft, Bayerwerk, Fed. Rep. of Germany

[21] Appl. No.: 331,412

[22] Filed: Dec. 16, 1981

[30] Foreign Application Priority Data

Dec. 19, 1980 [DE] Fed. Rep. of Germany ....... 3047898

[51] Int. Cl.³ .............................................. C07C 118/00
[52] U.S. Cl. .................... 260/453 P; 560/24
[58] Field of Search ........................ 260/453 P; 560/24

[56] References Cited

U.S. PATENT DOCUMENTS

| | | | |
|---|---|---|---|
| 2,409,712 | 10/1946 | Schweitzer | 260/453 |
| 2,692,275 | 10/1954 | Bortnick | 216/453 |
| 2,713,591 | 7/1955 | Bortnick | 260/453 |
| 2,727,020 | 12/1955 | Melamed et al. | 260/80.3 |
| 3,734,941 | 5/1973 | Sydor | 260/453 P |
| 3,870,739 | 3/1975 | DeLaMater et al. | 260/453 P |
| 3,919,278 | 11/1975 | Rosenthal et al. | 260/453 P |
| 3,919,279 | 11/1975 | Rosenthal et al. | 260/453 P |
| 3,919,280 | 11/1975 | Rosenthal et al. | 260/453 P |
| 3,962,302 | 6/1976 | Rosenthal et al. | 260/453 P |
| 4,081,472 | 3/1978 | Tsumura et al. | 260/453 P |
| 4,195,031 | 3/1980 | Reichmann et al. | 260/453 P |

OTHER PUBLICATIONS

A. W. Hofman, Berichte der Deutschen Chemischen Gesellschaft, Year 1870, p. 653 et seq.
Maurice Metayer, Bull. Soc. Chim. France, Year 1951, p. 802 et seq.
Hugo Schiff, Berichte der Deutschen Chemischen Gesellschaft, Year 1870, p. 649 et seq.
Elizabeth Dyer and George C. Wright, (J. American Chemical Society, vol. 81, 1959, p. 2138 et seq.
J. Applied Polymer Science, vol. 16, 1972, p. 1213.

*Primary Examiner*—Dolph H. Torrence
*Attorney, Agent, or Firm*—Gene Harsh; Joseph C. Gil; Lyndanne M. Whalen

[57] ABSTRACT

A carbamic acid ester corresponding to the formula $R^1$—NH—CO—$OR^2$ is thermally cleaved to form isocyanate $R^1$—NCO and alcohol $R^2$—OH fractions. This cleavage is accomplished by boiling the carbamic acid ester, condensing the vapor given off in a first fractionation column, and condensing the vapor from the first fractionation column in a second fractionation column. The boiling of the carbamic acid ester is carried out in a manner such that the average dwell time in the reaction vessel is from 1 to 20 hours, the temperature is from 160° to 260° C. and the pressure is from 0.001 to 2 bar. The isocyanate fraction obtained by this cleavage process may be used as a starting material for a transurethanation reaction in which a lower boiling isocyanate $R^3$—NCO is produced. The radicals $R^1$, $R^2$, and $R^3$ are defined herein.

23 Claims, 3 Drawing Figures

PROCESS FOR THE CONTINUOUS THERMAL CLEAVAGE OF CARBAMIC ACID ESTERS AND PREPARATION OF ISOCYANATES FROM THE PRODUCTS THEREOF

BACKGROUND OF THE INVENTION

This invention relates to an improved process for the continuous thermal cleavage of N-monosubstituted carbamic acid alkyl esters and a process for the preparation of isocyanates which at normal pressure have a boiling point at least 50° C. below that of the isocyanate obtained from the thermal cleavage.

The thermal cleavage of N-monosubstituted carbamic acid alkyl esters has long been known. As demonstrated by the work of A. W. Hoffmann (Berichte der Deutschen Chemischen Gesellschaft, Year 1870, page 653 et seq) and M. Metayer (Bull. Soc. Chim. France, Year 1951, page 802 et seq.), these cleavage reactions are reversible, i.e. when the hot reaction mixtures cool, the isocyanates recombine with the alcohols to form carbamic acid esters. Special measures are therefore required if the isocyanates and alcohols obtained from the thermal cleavage of carbamic acid esters are to be recovered separately.

U.S. Pat. No. 2,409,712 describes a process in which the recombination of isocyanates and alcohols after the thermal cleavage of carbamic acid esters is prevented by immediate separation of the cleavage products. Such separation may be accomplished by introduction of the gases of thermolysis into a cyclohexane-water mixture or by rapid distillation. Although this process is suitable for the discontinuous preparation of isocyanates on a laboratory scale, it is not suitable for a commercial process because immediate separation of the cleavage products is extremely difficult from a technical standpoint. Moreover, the process described in this patent provides only moderate yields of isocyanate, as can be seen from the examples given therein.

It is also known that when N-monosubstituted carbamic acid esters are subjected to heat, they may undergo partial or complete irreversible decomposition. As the investigations of H. Schiff (Berichte der Deutschen Chemischen Gesellschaft, Year 1870, page 649 et seq.) and of E. Dyer and G. C. Wright (J. Amer. Chem. Soc. Volume 81, Year 1959, page 2138 et seq.) have shown the decomposition products may include substituted ureas, biurets, carbodiimides, isocyanurates, secondary amines, olefines and/or carbon dioxide. These decomposition reactions not only reduce the isocyanate yield but may also interfere with processing equipment. For example, difficulty soluble ureas or isocyanaurates may cause blockages in pipes. Carbon dioxide and gaseous olefins may heavily charge the distillation columns with gas. Lastly, basic materials which form as by-products may catalyze irreversible decomposition reactions of carbamic acid esters.

Various processes have been developed in an effort to suppress the decompositions which accompany thermal cleavage. One approach is to reduce the amount of heat used in the cleavage reaction. Such processes are, however, disadvantageous in that the thermal cleavage must generally be carried out in the presence of a catalyst since the volume/time yields would otherwise be too low. In any event, the cleavage of carbamic acid esters into isocyanates and alcohols is by its nature a process in which the application of at least a minimum amount of heat is unavoidable, whether catalysts are used or not.

Processes for the preparation of isocyanates by thermal cleavage of carbamic acid esters in the presence of basic catalysts have been described in U.S. Pat. Nos. 2,713,591; 2,692,275 and 2,727,020 and in Japanese Patent Application No. 54-88201 (1979). Use of basic catalysts may, however, lead to increased irreversible decomposition reactions of carbamic acid esters. (See e.g., J. Appl. Polym. Sci., Volume 16, Year 1972, page 1213). Processes using basic catalysts can therefore result in acceptable isocyanate yields only if the carbamic acid esters used are protected against decomposition by means of suitable substituents.

Another possible method for suppressing side reactions in the thermal cleavage of carbamic acid esters is dilution of the carbamic acid esters and/or the gases of thermolysis with inert diluents. In the processes described in U.S. Pat. No. 3,919,279, German Offenlegungsschrift No. 2,635,490 and Japanese Patent Applications 54-39002 (1979) and 54-88222 (1979), thermal cleavage of carbamic acid esters is carried out in inert solvents, optionally in the presence of certain catalysts. In the processes described in German Auslegeschriften Nos. 2,421,503 and 2,526,193, carrier gases are used in addition to inert solvents, optionally in the form of vaporized low boiling solvents.

The use of solvents in the thermal cleavage of carbamic acid esters does, however, present serious difficulties. The solvent must be stable under the conditions of thermolysis and it must also be inert with respect to isocyanates. The solvent must also be readily miscible with carbamic acid esters and have a vapor pressure at the temperatures employed low enough that it will remain substantially in the liquid phase during thermolysis. These requirements severely limit the choice of solvents. Suitable inexpensive solvents are difficult to find, particularly for the cleavage of carbamic acid esters which have a high molecular weight. Moreover, the use of solvents reduces the volume/time yields of isocyanates. Yet another disadvantage is that when high boiling solvents are used, it is difficult to separate the pure components (residues of isocyanate and carbamic acid ester, and solvent) from the residue in the liquid reaction mixtures by distillation. (See e.g. German Auslegeschrift No. 2,530,001). Further, the working-up and storing of inert diluents entails considerable additional capital expenditure.

U.S. Pat. Nos. 3,734,941 and 3,870,739 describe processes in which carbamic acid esters are split at high temperatures (400° to 600° C. and 350° to 550° C.) in the gaseous phase. One disadvantage of such a process is that the dwell times of the gases in the high temperature range must be short to avoid extensive decomposition of the carbamic acid esters and/or the isocyanates formed due to the high temperature which would otherwise occur in spite of the dilution by the gaseous phase. Short dwell times, however, result in correspondingly low yields of isocyanates. Moreover, this process entails considerable technical difficulty since gases are difficult to heat and cool within a short time due to their low thermal conductivity.

SUMMARY OF THE INVENTION

It is an object of the present invention to provide a process for the thermal cleavage of carbamic acid esters.

It is another object of the present invention to provide a process for the thermal cleavage of carbamic acid esters and for the separation of the thus-produced fractions.

It is also an object of the present invention to provide a continuous process for the thermal cleavage of carbamic acid esters into an isocyanate and an alcohol fraction and for the separation of these fractions.

It is a further object of the present invention to provide a technically practical process for the thermal cleavage of N-monosubstituted carbamic acid alkyl esters into fractions containing isocyanate and alcohol which process does not require use of a solvent, of a catalyst or of extremely high temperatures.

It is yet another object of the present invention to provide a process in which the isocyanate fraction obtained from the thermal cleavage of a carbamic acid ester may be used to produce another isocyanate having a boiling point at least 50° C. below that of the isocyanate produced by thermal cleavage.

These and other objects which will be apparent to those skilled in the art are accomplished by a thermal cleavage process in which a carbamic acid ester is continuously introduced into a reaction vessel in which the ester is boiled to partially cleave that ester into isocyanate and alcohol.

The gas given off from the reaction vessel is then partially condensed in a first fractionation column. The gaseous product from this first fractionation column is then partially condensed in a second fractionation column. The higher boiling of the isocyanate and alcohol fractions is condensed in the second fractionation column while the lower boiling fraction is given off as a gas. The thus-produced isocyanate fraction may then be used to produce a lower boiling isocyanate.

DETAILED DESCRIPTION OF THE INVENTION

Figure 1:
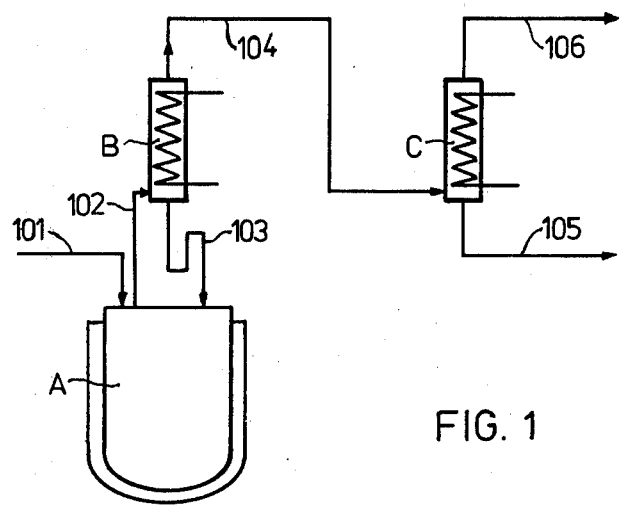
FIGS. 1 and 2 illustrate typical apparatus which may be used to thermally cleave a carbamic acid ester in accordance with the present invention.

The present invention thus relates to a process for the continuous thermal cleavage of carbamic acid esters which have a boiling point (at atmospheric pressure) of at least 200° C., corresponding to the general formula $$R^1-NH-CO-OR^2$$

wherein
 represents an aliphatic hydrocarbon group having a total of from 1 to 18 carbon atoms, which may be olefinically unsaturated and/or may carry inert substituents; a cycloaliphatic hydrocarbon group having a total of from 3 to 18 carbon atoms which may be olefinically unsaturated and/or may carry inert substituents; an araliphatic hydrocarbon group having 7 to 18 carbon atoms which may carry inert substituents; or an aromatic hydrocarbon group having from 6 to 18 carbon atoms which may carry inert substituents; and
$R^1$ represents a group such as may be obtained by removal of the hydroxyl group from a primary or secondary aliphatic, cycloaliphatic or araliphatic alcohol whose boiling point (at atmospheric pressure) is at least 50° C. below or above the boiling point of the isocyanate $R^1-NCO$ corresponding to the group $R^1$.

The invention also relates to the separation of the cleavage products by distillation into a fraction containing an isocyanate of the formula $R^1-NCO$ and a fraction containing an alcohol of the formula $R^2-OH$.

In the process of the present invention, a carbamic acid ester which is to be split is continuously introduced into a reaction vessel equipped with a fractionation column. The ester in the reaction vessel is kept boiling for a period such that the average dwell time is from 1 to 20 hours at a temperature within the range of 160° to 260° C. and a pressure of from 0.001 to 2 bar. Under these conditions, the carbamic acid ester undergoes partial cleavage and a product mixture containing carbamic acid ester, isocyanate and alcohol is continuously evaporated. The thus-produced vapor is then partially condensed in a first fractionation column. The condensate from this column will generally contain substantial amounts of undecomposed carbamic acid ester which are recycled to the reaction vessel. The gaseous product mixture escaping above the first fractionation column is then partially condensed in a second fractionation column to form a condensate containing (i) residues of carbamic acid ester and (ii) either the isocyanate $R^1-NCO$ boiling at a higher temperature than the alcohol $R^2-OH$ or the alcohol boiling at a higher temperature than the isocyanate. The lower boiling of the alcohol and the isocyanate escapes from the second fractionation column in gaseous form and may be in admixture with small portions of carbamic acid ester.

The present invention also relates to a process for the production of a monoisocyanate corresponding to the formula $R^3-NCO$ from the mixture containing isocyanate of the formula $R^1-NCO$ and carbamic acid ester of the formula $R^1-NH-CO-OR^2$ obtained as condensate of the second fractionation column in the above-described cleavage process and from a carbamic acid ester of the general formula $R^3-NH-CO-OR^2$. The monoisocyanate $R^3-NCO$ has a boiling point (at atmospheric pressure) at least 50° C. below the boiling point of the isocyanate $R^1-NCO$ and the radical $R^3$ has the meaning indicated above for $R^1$ except for this restriction with respect to boiling point. Specifically, the condensate from the second fractionation column in the above-described cleavage process and the carbamic acid ester of the formula $R^3-NH-CO-OR^2$ are continuously reacted in a molar ratio of carbamic acid ester $R^3-NH-CO-OR^2$ to isocyanate $R^1-NCO$ of from 1:1 to 1:10 in a reaction vessel or a series of reaction vessels. This reaction is carried out at a temperature of from 50° to 200° C. The pressure is adjusted so that the reaction mixture boils. The gaseous product mixture given off during this boiling includes isocyanate $R^3-NCO$ and may also have small amounts of the isocyanate $R^1-NCO$ and of the carbamic acid ester $R^3-NH-CO-OR^2$ present. This gaseous product mixture is continuously removed from the reaction vessel or vessels and the isocyanate $R^3-NCO$ may be separated from this product mixture in virtually pure form by distillation. Any distillation residue may then be returned to the reaction vessel or vessels. A liquid product mixture enriched in carbamic acid ester of the formula $R^1-NH-CO-OR^2$ may be continuously removed from the reaction vessel or from the last reaction vessel of the series and recycled to a reaction vessel in which that ester is subjected to thermal cleavage. Prior to introduction to the vessel in which the thermal cleavage is carried out, it is advantageous to subject the carbamic acid ester containing mixtures to a stripping distillation in which the isocyanate $R^1$—NCO present therein is partially or completely separated and the carbamic acid ester $R^3$—NH—CO—$OR^2$ present is separated. The thus-separated isocyanate and carbamic acid ester may then be returned to the reaction vessel or vessels in which the isocyanate $R^3$—NCO is formed. The carbamic acid esters which may be used as starting materials for the process according to the invention have a boiling point (at atmospheric pressure) of at least 200° C. and correspond to the general formula $$R^1\text{—NH—CO—}OR^2$$

wherein $R^1$ and $R^2$ have the meaning indicated above.

Particularly suitable carbamic acid esters are those corresponding to the above formula in which the group $R^2$ is the residue of an alcohol which has a boiling point at normal pressure at least 70° C. above or below the boiling point of the isocyanate $R^1$—NCO. In the process of the present invention, those carbamic acid esters corresponding to the above formula in which the boiling points of the cleavage products $R^1$—NCO and $R^2$—OH differ from each other by at least 50° C., (preferably at least 70° C. at normal pressure) should be used. Particularly preferred carbamic acid esters for the process according to the invention are those corresponding to the above general formula in which the hydrocarbon group $R^2$ contains from 1 to 6 carbon atoms if the hydrocarbon group $R^1$ contains from 6 to 18 carbon atoms and those in which the group $R^2$ contains from 6 to 14 carbon atoms when the group $R^1$ contains from 1 to 5 carbon atoms.

Suitable carbamic acid esters which may be used as starting compounds for the process of the present invention include: N-methylcarbamic acid-hexyl ester, -(1-methyl-pentyl)-ester, -(2-ethylbutyl)-ester, -2(2-isopropoxy-ethyl)-ester; N-ethylcarbamic acid-hexylester, -cyclohexylester, -(1-methyl-pentyl)-ester, -(2-butoxy-ethyl)-ester; N-propylcarbamic acid -heptyl ester, -(1-methylheptyl)-ester, -(2-ethyl-hexyl)-ester, -(2-acetoxyethyl)-ester; N-isopropylcarbamic acid-hexylester, -(2-butoxy-ethyl)-ester, -heptylester, -(2-ethylhexyl)-ester; N-(2-methoxy-ethyl)-carbamic acid-octylester, -(2-(2-ethoxy-ethoxy)-ethyl)-ester, -(2-phenyl-ethyl)-ester, -decylester; N-(2-cyanoethyl)-carbamic acid-ethylester, -propylester, -butylester, -(2-methoxy-ethyl)-ester; N-butylcarbamic acid-octyl ester, -(2-(2-methoxy-ethoxy)ethyl)-ester, -(2-(2-ethoxy-ethoxy)-ethyl)-ester, -(2-phenyl-ethyl)-ester; N-tert.-butylcarbamic acid-hexylester, -cyclohexylester, -(2-ethyl-butyl)ester, -(2-acetoxy-ethyl)-ester; N-pentylcarbamic acid-methyl ester, -(2-(2-ethoxy-ethoxy)-ethyl)ester, -(2-phenyl-ethyl)-ester, -decylester; N-neopentylcarbamic acid-methyl ester, -(2-ethylhexyl)-ester, -octylester, -(2-phenyl-ethyl)-ester; N-hexylcarbamic acid-methyl ester, -ethylester, -isopropylester, -decylester; N-(2-ethyl-hexyl)carbamic acid-ethyl ester, -propylester, -isopropylester, -(2-methyl-propyl)-ester; N-octylcarbamic acid-methyl ester, -isopropylester, -(1-methylpropyl)-ester, -butylester; N-heptadecylcarbamic acid-ethylester, -isopropylester, -butylester, -(2-ethoxy-ethyl)-ester; N-allylcarbamic acid-cyclohexyl ester, -(2-butoxy-ethyl)-ester, -(1-methylheptyl)-ester, -(2-ethyl-hexyl)-ester; N-(3-methylallyl)-carbamic acid-(2-butoxy-ethyl)-ester, -heptylester, -(2-ethylhexyl)-ester, -octylester; N-cyclopentylcarbamic acid-methyl ester, -ethylester, -(2-phenyl-ethyl)-ester, -decylester; N-cyclohexylcarbamic acid-methylester, -ethylester, -isopropylester, -(2-methyl-propyl)-ester; N-(cyclohexyl-cyclohexyl)-carbamic acid-ethylester, -isopropylester, -butylester, -(2-ethoxyethyl)-ester; N-(2-methyl-hex-1-enyl)-carbamic acid methyl ester, -ethylester, -propylester, -(1-methyl-propyl)-ester; N-benzylcarbamic acid-methyl ester, -ethylester, -propylester, -isopropylester; N-(2-phenyl-ethyl)-carbamic acid-ethylester, -butylester, -(2-methoxy-ethyl)ester, -(3-methyl-butyl)-ester; N-phenylcarbamic acid-methylester, -ethylester, -propylester, -isopropylester; N-(4-chlorophenyl)-carbamic acid-ethylester, -propylester, -butylester, -(2-methoxy-ethyl)ester; N-(3,4-dichlorophenyl)carbamic acid-ethylester, -butylester, -(2-methyl-propyl)-ester, -(2-ethoxy-ethyl)-ester; N-3-tolyl-carbamic acid-methylester, -ethylester; -isopropylester, -(2-methylpropyl)-ester; N-(3-chloro-4-methyl-phenyl)-carbamic acid-ethylester, -butylester, -(2-methoxy-ethyl)ester, -(3-methyl-butyl)-ester; N-(4-cyclohexyl-phenyl)-carbamic acid-ethylester, -butylester, -pentylester, -(2-ethoxy-ethyl)-ester; N-(3-trifluoromethyl-phenyl)-carbamic acid-methylester, -ethylester, -propylester, -isopropylester; N-(4-benzyl-phenyl)-carbamic acid-ethylester, -butylester, -(2-ethoxy-ethyl)-ester, -hexylester; N-(3-cyanophenyl)-carbamic acid-methylester, -isopropylester, -(2-methoxy-ethyl)-ester, -pentylester; N-(4-methoxycarbonyl-phenyl)-carbamic acid-ethylester, -propylester, -butylester, -(2-ethoxy-ethyl)-ester, N-1-naphthyl-carbamic acid-methylester, -(2-methyl-propyl)-ester, -pentylester, -hexylester.

The carbamic acid esters which are suitable starting compounds for the process according to the invention may be prepared by known chemical methods. Such known methods include: (1) reaction of the corresponding primary amines with chloroformic acid ester; (2) carbonylation of the corresponding nitro compounds in the presence of alcohols; and (3) the reaction of N,N'-disubstituted ureas with alcohols. The carbamic acid esters may, of course, also be prepared by any other method desired.

The process of the present invention is particularly advantageous in that thermal cleavage results in optimum yields of the cleavage products (i.e., isocyanate and alcohol) and minimum quantities of by-products if the carbamic acid esters are continuously fed into a reaction vessel, heated to the cleavage temperature in this vessel for comparatively long dwell times, and care is taken to ensure that by adjustment of a suitable pressure the cleavage products are continuously removed from the reaction mixture in the gaseous form together with any undecomposed carbamic acid ester. To achieve maximum yields, this gaseous product mixture should be partially condensed in a fractionation column in a manner such that the condensate discharged from the column and returned to the reaction vessel consists substantially of undecomposed carbamic acid ester and that the gaseous product mixture escaping at the head of this fractionation column is partially condensed in a second fractionation column in a manner such that the condensate obtained from it is a mixture of residues of carbamic acid ester and the higher boiling of the isocyanate and alcohol fractions. The alcohol or isocyanate fraction which boils at the lower temperature escapes in gaseous form from the head of the second fractionation column.

It must be regarded as extremely surprising that both the thermal cleavage of carbamic acid esters and the subsequent separation of the cleavage products (i.e., isocyanate and alcohol) by the process of the present invention can be carried out with high yields and minimal formation of by-products. Such results are particularly surprising in view of Examples 2, 12 and 13 (Comparison Examples) of German Auslegeschrift No. 2,421,503 which show that the heating of N-monosubstituted carbamic acid alkyl esters to 200°-260° C. for 3 hours or for one hour, respectively, results in the formation of substantial amounts of unusable by-products.

The effectiveness with which the gaseous mixtures containing carbamic acid ester, isocyanate and alcohol can be separated in the process of the present invention is also surprising. This is evidenced by the fact that when one uses an efficient distillation column (optionally with means for removal by a side stream) instead of the two fractionation columns to separate the products, a far smaller quantity of cleavage products is obtained (sometimes none at all) and the product obtained consists completely or virtually completely of carbamic acid ester.

The process of the present invention is described in more detail with reference to FIG. 1.

FIG. 1 illustrates one example of an apparatus suitable for carrying out the thermal cleavage process of the present invention. The process of the present invention is not, however, limited to use of the apparatus illustrated in FIG. 1.

In FIG. 1, A denotes a reaction vessel equipped with heating jacket, B and C each represent cooling coils used as fractionation columns. When the process of the present invention is carried out in the apparatus illustrated in FIG. 1, the carbamic acid ester is continuously fed into the reaction vessel A through pipe (101) and heated therein. A mixture containing carbamic acid ester, isocyanate and alcohol is continuously removed in gaseous form from the reaction vessel A through the pipe (102), to the fractionation column B in which the mixture is partially condensed. The condensate, consisting mainly of carbamic acid ester, is returned to the reaction vessel A through the pipe (103). The gaseous product mixture escaping from the head of the fractionation column B through pipe (104) is introduced into the fractionation column C in which that mixture is partially condensed. A condensate consisting substantially of residues of carbamic acid ester and of isocyanate boiling at a higher temperature than the alcohol or of alcohol boiling at a higher temperature than the isocyanate is continuously removed through pipe (105). The gaseous product escaping at the head of the fractionation column C through pipe (106) consists substantially of alcohol boiling at a lower temperature than the isocyanate or of isocyanate boiling at a lower temperature than the alcohol, optionally mixed with proportionally small amounts of carbamic acid ester.

It is not an essential feature of the process according to the invention that the two fractionation columns shown in FIG. 1 be separated and connected through a pipe. It may even be advantageous to arrange them in a single apparatus one above the other, the condensate from the upper fractionation column being advantageously collected on a tray situated between the two fractionation columns.

Nor is it important for the process of the present invention that the gaseous and liquid streams of product should flow in two separate pipes from reaction vessel A to fractionation column B and conversely. The two product streams may also be passed through a single pipe of suitably large cross-section. The fractionation column B could, of course, be directly attached to the reaction vessel A so that no pipes need be provided to connect the two apparatuses.

When carrying out the process according to the present invention, the temperature of the reaction mixture in reaction vessel A should generally be from 160° to 260° C., preferably from 180° to 240° C. It is advantageous to adjust the reaction temperature to obtain maximum volume/time yields of cleavage products with minimum formation of unusable by-products. This optimum reaction temperature varies for different carbamic acid esters. This optimum temperature which depends on the nature of the groups $R^1$ and $R^2$, may be readily determined in each case by techniques known to those in the art. The optimum reaction temperature also depends upon the nature and quantity of the catalyst and/or stabilizers added. Cleavage of the carbamic acid esters may, of course, also be carried out at a temperature other than the optimum reaction temperature within the temperature range indicated above.

When carrying out the process of the present invention, the pressure in the reaction vessel A may be adjusted so that the reaction mixture boils. This pressure is from 0.001 to 2 bar, preferably from 0.01 to 1 bar. The amount of pressure is dependent upon the reaction temperature, the vapor pressure of the carbamic acid ester to be split, and the cleavage products (i.e., isocyanate and alcohol).

The pressure in the fractionation columns should generally be as high as or slightly lower (due to pressure loss in the pipes and apparatus) than reaction vessel A. If desired, however, the fractionation columns B and C may be adjusted to a lower pressure than that of reaction vessel A.

When carrying out the process of the present invention, the average dwell time in reaction vessel A of the carbamic acid ester being split is from 1 to 20 hours, preferably from 3 to 10 hours. The average dwell time may be adjusted to different values within certain limits, but the resulting rate of cleavage is then altered correspondingly. The dwell time should preferably be chosen so that maximum volume/time yields of cleavage products, isocyanate and alcohol, are achieved with minimum formation of unusable by-products. This optimum dwell time depends upon the groups $R^1$ and $R^2$ of the carbamic acid ester which is to be split, the reaction temperature, and the nature and quantity of any catalyst and/or stabilizer added. This optimum dwell time, like the optimum reaction temperature, may be determined for each carbamic acid ester by techniques known to those in the art. The thermal cleavage of carbamic acid esters by the process according to the invention may, of course, also be carried out within the range indicated in a manner such that the average dwell time is other than the optimum.

It is not essential to the process of the present invention that a proportionately large quantity of undecomposed carbamic acid ester should be removed in gaseous form from the reaction vessel A, condensed in the first fractionation column and returned to reaction vessel A. In fact, it is generally advantageous to keep the quantity of undecomposed carbamic acid ester recirculated as low as possible since recirculation entails expenditure of significant amounts of energy. The only essential condition with respect to the amount of carbamic acid ester employed is that the quantity of gaseous product mixture removed from the reaction vessel A should be sufficient to ensure that at least a small proportion of this gaseous mixture should be able to condense in fractionation column B to form a liquid containing substantial amounts of carbamic acid ester. The quantity of condensate formed in fractionation column B is generally from 5 to 80 wt. %, preferably from 10 to 50 wt. % (based on the total quantity of vapors leaving the reaction vessel A, but not including vapors of any high boiling auxiliary solvents used and condensed in fractionation column B). The quantity of condensate formed may easily be adjusted within the ranges mentioned above by using an appropriate temperature and pressure (i.e., one within the above-mentioned range) in the reaction vessel A and by the cooling power of the fractionation column B. The cooling fluid in the fractionation column B should be between the boiling point of the carbamic acid ester being cleaved and the boiling point of the higher boiling of the isocyanate and the alcohol at the pressure employed. If the cooling fluid of the fractionation column is maintained at such a temperature, at least 70 wt. % (preferably at least 85 wt. %) of the carbamic acid ester leaving the reaction vessel in a gaseous form and at most 35 wt. % (preferably not more than 10 wt. %) of the higher boiling of the alcohol and the isocyanate cleavage products leaving the reaction vessel in a gaseous form will condense in the fractionation column B.

The vapor leaving the fractionation column B, is a mixture of alcohol, isocyanate and small quantities of carbamic acid ester. This gaseous mixture is separated in fractionation column C into a condensate made up of small quantities of carbamic acid ester and the higher boiling of the isocyanate and the alcohol cleavage products. A gaseous phase composed primarily of the lower boiling of the alcohol and the isocyanate cleavage products is given off from the fractionation column. It is advantageous to maintain the cooling fluid in the fractionation column C at a temperature between the boiling point of the isocyanate and of the alcohol cleavage products at the pressure employed. The cooling fluid in fractionation columns B and C may, however, also be adjusted to temperatures substantially lower than those described above. If such lower temperatures are employed, the partial condensation of the vapors fed into the fractionation columns may be achieved by controlled overloading of the heat exchangers.

The fractionation columns used in the process of the present invention are generally heat exchangers operated with either liquid or gaseous cooling fluids such as water, oil acting as heat carrier, or air.

The process of the present invention may be accompanied by the formation of a small quantity of high boiling by-products which accumulate in the reaction vessel A. These by-products, which will be referred to hereinafter as residue, may be separated from the reaction mixture by various methods known to those in the art. One possible method for removing the residue consists of stopping the supply of fresh carbamic acid ester into the reaction vessel A when the concentration of residue in the reaction mixture has become too high, removing the volatile constituents of the reaction mixture from the reaction vessel A by distillation, and discharging the residue left behind. The residue may also be flushed out of the reaction mixture continuously if this appears to be necessary or desirable. This flushing may be achieved, for example, by continuously removing liquid reaction mixture from reaction vessel A, freeing it from residue by a stripping distillation and then returning the residue-free liquid into reaction vessel A. The separation of residue may, of course, also be carried out by filtration.

The process of the present invention is preferably carried out without the aid of auxiliary solvents although it is possible in principle to carry out the thermal decomposition in reaction vessel A in the presence of inert liquids. Inert liquids are those which are virtually non-volatile at the given temperature and pressure conditions or which condense to a large extent in the fractionation column B under the given temperature and pressure conditions. Such inert liquids may be used to plasticize high melting residues. Suitable liquids of this type include aromatic and araliphatic hydrocarbons having at least 10 carbon atoms and optionally carrying inert substituents, diarylethers, diarylsulphones and triarylphosphates.

The thermal cleavage of carbamic acid esters by the process of the present invention may be accelerated by use of suitable catalysts such as Lewis acids (see Houben-Weyl, Methoden der Organischen Chemie, Volume 4, part 2, page 6), e.g. $BF_3$, $BCl_3$, $B(OC_2H_5)_3$, $B(OC_4H_9)_3$, $AlCl_3$, $AlBr_3$, $SnCl_4$, dibutyl tin oxide, $SbCl_5$, $TiCl_4$, $TiBr_4$, $FeCl_3$, cobalt octoate, $ZnCl_2$, zinc octoate or CuCl. Mixtures of several such compounds may also be used as catalysts. The catalyst, if used at all, should generally be added to the reaction mixture at a concentration of from 0.001 to 2 wt. %, preferably from 0.01 to 1 wt. %. If a catalyst is used, the same cleavage rate that is obtained without a catalyst can generally be achieved with a shorter dwell time and/or a lower reaction temperature.

When carrying out the process of the present invention, the formation of unwanted by-products can be reduced by the addition of stabilizers. Examples of suitable stabilizers include carboxylic acid chlorides such as acetyl chloride, butyric acid chloride, stearic acid chloride, adipic acid dichloride, benzoyl chloride, phthalic acid dichloride and terephthalic acid dichloride; and/or sulfonic acid chlorides such as methanesulfonic acid chloride, benzenesulfonic acid chloride and p-toluenesulfonic acid chloride; and/or sulfonic acid esters such as methanesulfonic acid butyl ester, octanesulfonic acid ethyl ester, benzenesulfonic acid methyl ester, p-toluene sulfonic acid ethyl ester and 4-ethoxycarbonylbenzene sulfonic acid ethyl ester; and/or alkylating compounds such as n-hexylchloride, n-hexyliodide, n-octylbromide, dimethylsulfate and diethylsulfate. Mixtures of several compounds may also be used as a stabilizer. The stabilizer, if used, should be added to the reaction mixture at a total concentration of from 0.001 to 2 wt. %, preferably from 0.01 to 1 wt. %.

The monoisocyanate $R^1$—NCO prepared by the process of the present invention can be isolated from the fractions in which it is present by distillation and thus obtained in pure form. These monoisocyanate-containing fractions are removed as gaseous product mixture from the head of the fractionation column C if the alcohol $R^2$—OH obtained by cleavage boils at a higher temperature than the isocyanate $R^1$—NCO or as condensate from the fractionation column C if the isocyanate $R^1$—NCO prepared by cleavage boils at a higher temperature than the alcohol $R^2$—OH. These fractions contain substantial amounts of the isocyanate $R^1$—NCO, minor quantities of carbamic acid ester $R^1$—NH—CO—$OR^2$ and optionally small quantities of allophanate $R^1$—NH—CO—$NR^1$—CO—$OR^2$ which may be formed by molecular addition of the isocyanate $R^1$—NCO to the carbamic acid ester $R^1$—NH—CO—$OR^2$. Distillative separation of the fractions containing the isocyanate may be carried out by methods known to those in the art such as use of distillation columns.

The distillation residue obtained when isolating the isocyanate $R^1$—NCO in pure form is made up of carbamic acid ester and may also include residues of isocyanate. It may therefore be advantageous to feed these residues to the reaction vessel A where they may be subjected to the cleavage process.

The alcohol $R^2$—OH may also be obtained in pure form by distillation from the fractions containing the alcohol $R^2$—OH prepared by the process of the present invention. These alcohol-containing fractions, which are removed by fractionation column C either as condensate or as gaseous product mixture, consist primarily of the alcohol $R^2$—OH and minor quantities of carbamic acid ester $R^1$—NH—CO—$OR^2$. Separation of these fractions by distillation may be carried out by methods known in the art, for example by use of separating columns. The distillation residues obtained, which are mainly carbamic acid ester and possibly residues of alcohol, may be returned to reaction vessel A to be again subjected to cleavage.

Figure 2:
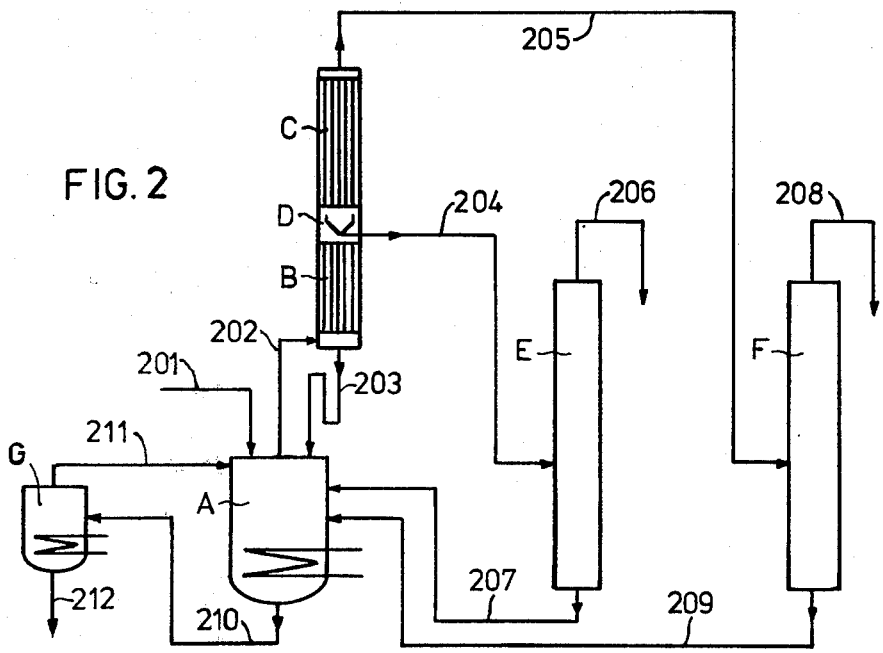

The process of the present invention for the preparation of monoisocyanates (including the recycling of carbamic acid ester containing residues) will be described with reference to FIG. 2 which illustrates an apparatus suitable for the preparation of isocyanates $R^1$—NCO. The process according to the invention is, however, in no way restricted to the use of the specific apparatus illustrated in FIG. 2. In FIG. 2, A represents a reaction vessel equipped with immersion evaporator; B and C each represent nests of tubes used as fractionation columns; D represents a discharge tray; E and F represent distillation columns; and G represents a distillation vessel equipped with immersion evaporator.

In the apparatus represented in FIG. 2, the carbamic acid ester is continuously fed into reaction vessel A through pipe (201) and heated therein. A gaseous mixture is continuously removed from reaction vessel A through pipe (202) and delivered to the fractionation column B to be partially condensed therein. The condensate is returned to reaction vessel A through pipe (203) while the gaseous mixture leaving the head of the fractionation column B enters the fractionation column C where it is partially condensed. The condensate reaching the discharge tray D of the fractionation column C flows through pipe (204) into distillation column E where it is separated by distillation. The head product removed through pipe (206) is either pure isocyanate boiling at a higher temperature than the alcohol or pure alcohol boiling at a higher temperature than the isocyanate. The sump product discharged through pipe (207) is returned to the reaction vessel A. The gaseous head product removed from fractionation column C through pipe (205) is transferred to the distillation column F where it is separated by distillation. The lower boiling of the alcohol and the isocyanate is removed in pure form from column F through pipe (208). The pump product of column F is returned to reaction vessel A through pipe (209). At the same time, liquid product mixture is continuously removed from the sump of the reaction vessel A through the pipe (210) to be subjected to a stripping distillation in distillation vessel G. The distillate obtained in distillation vessel G is returned to reaction vessel A through pipe (211) while the residue is continuously removed from the bottom of the distillation vessel G through pipe (212).

As has already been explained above, if the process of the present invention is carried out using carbamic acid esters whose alcohol component boils at a lower temperature than the isocyanate component, the condensate obtained from fractionation column C is a mixture of isocyanate boiling at a higher temperature than the alcohol and minor quantities of carbamic acid ester. This mixture is not only suitable as a starting material for the preparation of the isocyanate $R^1$—NCO in pure form, but may also be used as a starting material for the preparation of isocyanates $R^3$—NCO. The isocyanates $R^3$—NCO at normal pressure have a boiling point at least 50° C. lower than the boiling point of the isocyanate $R^1$—NCO. Apart from this restriction with respect to boiling point, $R^3$ may have the same meaning as $R^1$.

When the above-described mixtures obtained as condensate of fractionation column C in the process of the present invention are used as a starting material for the preparation of the isocyanate $R^3$—NCO in accordance with the present invention, these mixtures are reacted with carbamic acid esters of the formula $R^3$—NH—CO—$OR^2$ to undergo transurethanation. The amounts in which the reactants are used in this reaction are such that from 1 to 10, preferably from 1.1 to 3 mol of isocyanate $R^1$—NCO are present for each mol of carbamic acid ester $R^3$—NH—CO—$OR^2$. The transurethanation is carried out at a temperature in the range of from 50° to 200° C., preferably from 80° to 180° C., under pressure conditions such that the reaction mixture boils. The gaseous product mixture formed is mainly isocyanate $R^3$—NCO, possibly small quantities of isocyanate $R^1$—NCO and possibly small quantities of carbamic acid ester $R^3$—NH—CO—$OR^2$. The isocyanate $R^3$—NCO may be obtained in pure form from this mixture by distillation. The carbamic acid ester $R^1$—NH—CO—$OR^2$ formed in the reaction of the isocyanate $R^1$—NCO put into the process may be continuously returned to reaction vessel A.

Although the preparation of isocyanates by such transurethanation reactions is known in principle (see German Pat. No. 1,207,378), the isocyanates used and exemplified in the process of this prior publication are higher functional polyisocyanates such as tolylene diisocyanate or polyisocyanates of the diphenylmethane series which must first be prepared by phosgenation of the corresponding amines. Such higher functionality polyisocyanates constitute valuable intermediate products for the production of polyurethanes. Further, the carbamic acid esters of higher boiling polyisocyanates formed in the process according to German Pat. No. 1,207,378 must be regarded as valueless waste product. In short, the process according to German Pat. No. 1,207,378 has the disadvantages of requiring the use of valuable products and the disposal of unusable reaction products. In contrast, the process of the present invention enables low boiling monoisocyanates to be prepared by an inexpensive and economical process without the formation of valueless by-products. The isocyanate $R^1$—NCO required to produce the isocyanate $R^3$—NCO in accordance with the present invention is continuously obtained from the carbamic acid ester $R^1$—NH—CO—$OR^2$ by the cleavage process and at the same time carbamic acid ester is continuously being re-formed by the transurethanation reaction and may be reused. Consequently, the use of the products of the cleavage reaction of the present invention in such a transurethanation in which carbamic acid ester $R^3$—CO—$OR^2$ is split into isocyanate $R^3$—NCO and alcohol $R^2$—OH, is actually use of the isocyanate $R^1$—NCO as an auxiliary agent in circulation. Since the carbamic acid ester $R^1$—NH—CO—$OR^2$ is continuously formed again in the combined cleavage/transurethanation reactions of the present invention, it need only be replaced to the extent that losses occur (e.g., due to the formation of residues). Another advantage of the combination of cleavage and transurethanation reactions in the present invention is that such a process may be used for the conversion of those carbamic acid esters $R^3$—NH—CO—$OR^2$ into isocyanate and alcohol which are difficult or impossible to split by direct heat cleavage. An example of such a difficult to split isocyanate is one in which the boiling points of the isocyanate and alcohol obtained as cleavage products are similar or identical to those which distill without decomposition below 200° C.

When the cleavage process of the present invention is used in combination with the transurethanation reaction, the carbamic acid esters $R^1$—NH—CO—$OR^2$ used should be of the kind in which the isocyanate component $R^1$—NCO has a boiling point (at atmospheric pressure) at least 50° C. above the boiling point of isocyanate $R^3$—NCO and of the alcohol $R^2$—OH. The chemical reactions which take place in this combination of reactions may be represented by the following equations:

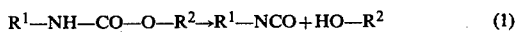   (1)

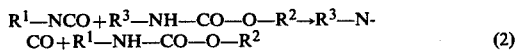   (2)

   (3)

It can be seen from these equations that carbamic acid esters which have the same alcohol component $R^2$—OH may be used in both the cleavage (equation (1)) and transurethanation (equation (2)) reactions of the present invention. As was discussed above, the transurethanation of the present invention may be carried out by using the condensate of fractionation column C which condensate contains the isocyanate $R^1$—NCO and minor quantities of carbamic acid ester $R^1$—NH—CO—$OR^2$. This carbamic acid ester, present in the condensate is inert under the transurethanation reaction conditions, is returned to reaction vessel A together with the carbamic acid ester of the same composition formed during the transurethanation reaction. When the isocyanate $R^1$—NCO is used in excess, based on the quantity of carbamic acid ester $R^3$—NH—CO—O—$R^2$, the product mixtures formed in the transurethanation still contain excess isocyanate $R^1$—NCO in addition to the volatile isocyanate $R^3$—NCO and the carbamic acid ester $R^1$—NH—CO—$OR^2$. After removal of the isocyanate $R^3$—NCO by distillation, this excess isocyanate $R^1$—NCO may also be removed from the carbamic acid ester $R^1$—NH—CO—$OR^2$ by distillation and may be used again in the thermal cleavage of the present invention, optionally together with the condensate from the fractionation column C.

Examples of carbamic acid esters $R^3$—NH—CO—$OR^2$ suitable for the use in the present invention include: N-methyl-carbamic acid-methylester, -ethylester; N-ethyl-carbamic acid-methylester, -isopropylester; N-propylcarbamic acid-ethylester, -isopropylester; N-isopropylcarbamic acid-methylester, -ethylester; N-butylcarbamic acid-ethylester, -butylester; N-(2-methyl-propyl)-carbamic acid-isopropyl-ester, -butylester; N-(1-methylpropyl)-carbamic acid-methylester, -propylester; N-pentylcarbamic acid-butylester, -(2-methoxyethyl)-ester; N-(ethoxycarbonyl-methyl)-carbamic acid-ethylester, -hexylester; N-allylcarbamic acid-ethylester, -isopropylester; N-cyclobutylcarbamic acid-methylester, -butylester; N-benzylcarbamic acid-(2-methoxy-ethyl)-ester, -(2-ethoxy-ethyl)-ester; N-(3-nitro-phenyl)-carbamic acid-ethylester, -butylester.

Although the transurethanation reaction which takes place in the present invention may be carried out in the absence of a catalyst, it is frequently advantageous to accelerate the reaction with suitable catalysts. Examples of suitable catalysts include the Lewis acids already mentioned above with respect to the thermal cleavage process. Particularly suitable catalysts are boric acid trialkylesters having 1 to 18 carbon atoms in the alkyl groups, especially those of the formula $B(OR^2)_3$ (i.e., boric acid esters in which the alcohol component corresponds to the alcohol component of the carbamic acid ester).

If a Lewis acid is used as a catalyst, it may be used in the process as a solid bed catalyst, optionally on an inert carrier material, or it may be homogeneously dissolved in the liquid reaction mixtures. In homogeneous catalysis, the catalyst content in the reaction mixture should generally be from 0.01 to 10 wt. %, preferably from 0.1 to 8 wt. %. When volatile catalysts are used, it is advantageous to separate these catalysts by distillation from the liquid phase of the transurethanation reaction mixture before the reaction mixture or a portion thereof is returned to reaction vessel A. These catalysts separated by distillation may, of course, be used in subsequent transurethanation reactions.

The transurethanation reaction which takes place between the carbamic acid ester $R^3$—NH—CO—$OR^2$ and the condensate from fractionation column B containing the isocyanate $R^1$—NCO and the removal of gaseous isocyanate $R^3$—NCO may be carried out in a single reaction vessel. It is generally advisable, however, to carry out the reaction in a series of reaction vessels particularly if the boiling points of the isocyanates differ by little more than 50° C. The reaction temperatures of the individual reaction vessels in such a series may differ within the ranges mentioned above. The optimum reaction temperatures depend upon the nature of the starting materials and the nature and quantity of any catalyst used. These temperatures may be readily determined by techniques known to those in the art. The reaction may, of course, also be carried out at temperatures other than the optimum reaction temperatures provided that such other temperatures are within the above-described temperature ranges.

As was discussed above, the transurethanation reaction of the present invention should take place under pressure conditions at which the reaction mixtures boil. The pressure required is dependent upon the nature of the reaction products and upon the reaction temperature and should generally be within the range of from 0.001 to 2 bar, preferably from 0.01 to 1 bar. When a series of reaction vessels is employed, the pressures in the individual reaction vessels may be adjusted to differing values if desired. It is generally advantageous, however, to adjust the reaction vessels in such a series to the same pressure and, if necessary, to employ differing reaction temperatures.

The average dwell time of the reaction mixtures in the reaction vessel or reaction vessels also depends upon the nature of the starting materials used, the nature and quantity of any catalysts used, and the pressure and temperature conditions. The average dwell time may therefore vary within wide limits although it is generally from 0.1 to 10 hours, preferably from 0.5 to 5 hours.

Figure 3:
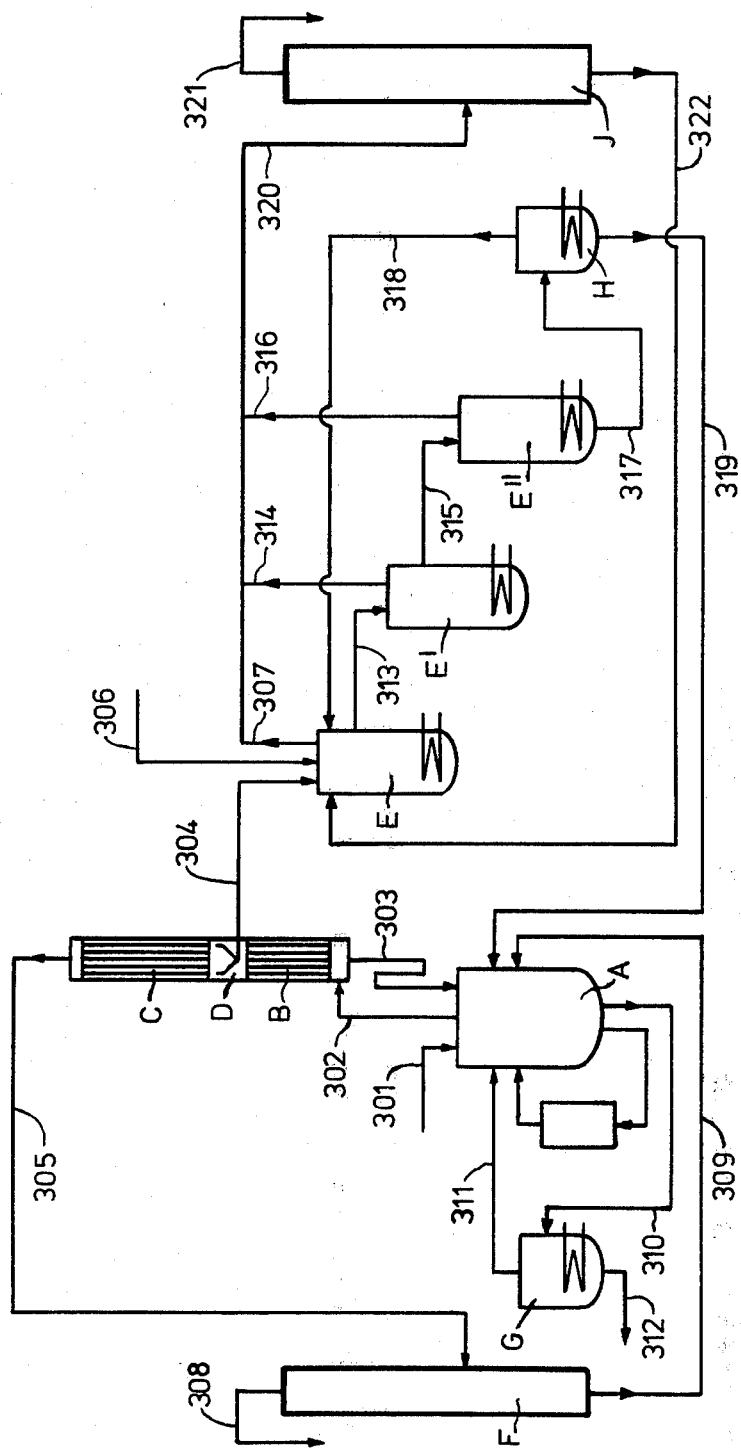
FIG. 3 illustrates an apparatus in which a carbamic acid ester is thermally cleaved and the isocyanate fraction thus-produced is used to make a lower boiling isocyanate.

FIG. 3 shows an apparatus in which the thermal cleavage process combined with the transurethanation of the present invention may be carried out continuously. The transurethanation reaction need not, however, be carried out in the apparatus illustrated in FIG. 3. In FIG. 3, the letters (A), (B), (C), (D), (F) and (G) have the same meaning as in FIG. 2 with the exception that the reaction vessel (A) in FIG. 3 is heated by means of a circulation evaporator. E, E' and E" denote a cascade of reaction vessels equipped with immersion evaporators. H denotes a distillation vessel equipped with immersion evaporator and J denotes a distillation column.

When the thermal cleavage is carried out simultaneously with the transurethanation reaction of the condensate obtained in fractionation column C, the cleavage of the carbamic acid ester $R^1$—NH—CO—$OR^2$ initially takes place in a manner analogous to the method described above with respect to FIG. 2. Therefore, in FIG. 3, the apparatus parts (A), (B), (C), (D), (F) and (G) perform the same function and the pipes (301) to (305) and (308) to (312) correspond to the pipes (201) to (205) and (208) to (212) of FIG. 2 in their function and in the streams of product transported by them.

In the transurethanation of the present invention using the condensates from fractionation column C removed from the discharge tray D, the said condensate is introduced into reaction vessel E through pipe (304) while carbamic acid ester $R^3$—NH—CO—$OR^2$ is introduced into reaction vessel E through pipe (306). The pipes (313) and (315) connect reaction vessel E to reaction vessels E' and E" in cascade formation. The pressure in reaction vessels E, E' and E" should be adjusted in each case so that the reaction mixtures heated to the given reaction temperatures boil. Gaseous product mixture is removed from the reaction vessels through pipes (307), (314) and (316) into the pipe (320) and transferred from into the distillation column J from which pure isocyanate $R^3$—NCO is continuously removed at the top through pipe (321) while the sump is returned to reaction vessel E through pipe (322). At the same time, liquid product mixture is continuously removed from reaction vessels E and E' through pipes (313) and (315), respectively, to be transferred to the next reaction vessel. Product mixture enriched with carbamic acid ester $R^1$—NH—CO—$OR^2$ is continuously removed from the sump of the reaction vessel E" through pipe (317) to be transferred to the distillation vessel H where it is stripped by distillation. The gaseous product mixtures thereby obtained are returned to reaction vessel E through pipe (318) while liquid product mixture is removed from the sump through pipe (319) to be returned to the reaction vessel A.

When the thermal cleavage process is carried out in combination with the transurethanation reaction according to the invention with the apparatus illustrated in FIG. 3, pure isocyanate $R^3$—NCO (by way of pipe 321) and pure alcohol $R^2$—OH (by way of pipe 308) are continuously obtained from carbamic acid ester $R^3$—NH—CO—$OR^2$ (from pipe 306). When the apparatus of FIG. 3 is in continuous operation, the quantity of carbamic acid ester $R^1$—NH—CO—$OR^2$ which must be supplied to the system by way of (301) is that corresponding to the quantity of by-products which are formed by side reactions and removed through (312). This quantity of by-products removed through (312) generally amounts to at the most 10 wt. % (based on the sum of process products removed through (308) and (321)).

It is not essential to the transurethanation reaction of the present invention that the separation by distillation of isocyanate $R^3$—NCO from the gaseous product mixture removed from the reaction vessel E or reaction vessels E, should be carried out by means of a separately arranged distillation column. This separation may also be carried out by means of a fractionation column. The distillation column or the fractionation column may also be directly attached to the reaction vessel E so that the distillation reflux returns directly to reaction vessel E. When a series of reaction vessels E is employed, the gaseous product mixtures removed from each reaction vessel may, of course, be separated by distillation, for example by means of fractionation columns or distillation columns directly attached to the reaction vessels.

The number of reaction vessels which may be combined to form a series is, of course, not critical. The liquid product mixture removed from the sump of the reaction vessel E or from the last reaction vessel of a series may be broken down by distillation. Such distillation is illustrated in FIG. 3, where the gaseous head product obtained from distillation vessel H is a gas phase enriched with isocyanates $R^1$—NCO. This gas phase rich in $R^1$—NCO is returned to the reaction vessel E while the sump of distillation vessel H contains carbamic acid ester $R^1$—NH—CO—O—$R^2$ which is returned to the cleavage reaction A. The distillative separation of the sump of the reaction vessel E or of the last reaction vessel may, however, be omitted if in the course of the reaction only a slight excess of isocyanate $R^1$—NCO has been used because the sump will be virtually pure carbamic acid ester $R^1$—NH—CO—$OR^2$.

When a series of reaction vessels E is used, it is not essential that in the transurethanation reaction the sump products from the column "J" and/or the distillates of the stripping distillation should be completely returned to the first reaction vessel E of the series as illustrated in FIG. 3. These streams of product may also be partly or completely returned to another reaction vessel E or into several other reaction vessels E.

It is essential to the transurethanation reaction of the present invention that during the course of the reaction, from 1 to 10, preferably from 1.1 to 3 mol of isocyanate $R^1$—NCO should be present for each mol of carbamic acid ester $R^3$—NH—CO—O—$R^2$. The total quantity of the isocyanate $R^1$—NCO is the sum of the isocyanate in the condensate of the fractionation column and any isocyanate $R^1$—NCO recycled as described above.

In the transurethanation reaction of the present invention, particularly when preparing low-boiling alkyl isocyanates $R^3$—NCO (such as methyl isocyanate), it may be advantageous to add a certain proportion (e.g., 30% by weight of the reaction mixture) of inert solvent to the reaction mixtures in reaction vessel E or in the reaction vessels E. The solvent should preferably be chosen so that its boiling point is between the boiling points of the isocyanates $R^1$—NCO and $R^3$—NCO. Such a solvent acts as a distillation aid in the process and promotes boiling of the reaction mixtures to form fractions containing isocyanate $R^3$—NCO. Any residue of such solvent in the liquid reaction mixtures introduced into reaction vessel A should be removed by distillation before the mixtures are fed into reaction vessel A (e.g., by stripping distillation).

The monoisocyanates which may be prepared by the process according to the invention are valuable starting materials for the production of plant protective agents or of pharmaceuticals.

The invention is further illustrated, but is not intended to be limited by the following examples in which all parts and percentages are by weight unless otherwise specified.

The following Examples illustrate the process according to the invention and should not be construed as limitations thereof.

EXAMPLES

Examples 1–17

The apparatus used in Examples 1 to 17 was similar to that illustrated in FIG. 1. The apparatus used in these Examples consisted of a 100 liter tank (reaction vessel A) with stirrer and heating jacket to which two cooling coils (B and C) used as fractionation columns were connected through heat insulated pipes. The cooling coils were charged with thermostatically controlled oil which acted as heat carrier. The volume of substance in reaction vessel A was adjusted to 80 liters and was kept constant by the rate of product feed through pipe (101), the heating power (A) and the cooling power of (B). The pressure in the fractionation columns was virtually the same as in reaction vessel A.

Any catalysts and/or stabilizer used was mixed with the carbamic acid ester introduced into reaction vessel A.

In Examples 1 to 13, the fractions containing isocyanate were obtained as partial condensates through pipe (105) from fractionation column C, and in Examples 14 to 17 they were obtained as gaseous mixtures through pipe (106) at the head of the fractionation column C.

Example 1 (see FIG. 1)

20.2 kg/h of molten N-cyclohexyl-carbamic acid ethyl ester were continuously introduced through pipe (101) into reaction vessel A. The reaction temperature in reaction vessel A was 225° C., the reaction pressure 1.0 bar. The gaseous product mixture escaping from the reactor through pipe (102) was partially condensed in fractionation column B which was supplied with oil adjusted to 180° C. The product mixture returned through pipe (103) to reaction vessel A contained 95.0 wt. % N-cyclohexyl-carbamic acid ethyl ester. Gaseous product mixture leaving through pipe (104) at the head of fractionation column B was introduced into fractionation column C which was supplied with oil adjusted to 95° C., and partially condensed there. 15.3 kg per hour of condensate containing 66.4% by weight of cyclohexylisocyanate were continuously removed through pipe (105) from fractionation column C while 4.5 kg/h of gaseous product mixture containing 86.3% by weight of ethanol continuously escaped through pipe (106) at the head of fractionation column C. The time of continuous production was 16 hours. The selectivity of thermal cleavage for the production of cyclohexyl isocyanate was 96 mol %.

Examples 2 through 17 were carried out in the same manner as in Example 1. The process parameters and results are summarized in Table 1.

Example 2

$R^1$—NH—CO—$OR^2$: N-phenyl-carbamic acid-ethyl ester
Catalyst: none
Stabilizer: none

Example 3

$R^1$—NH—CO—$OR^2$: N-phenyl-carbamic acid-ethyl ester
Catalyst: Di-n-butyl-tin dichloride
Stabilizer: none

Example 4

$R^1$—NH—CO—$OR^2$: N-phenyl-carbamic acid-ethyl ester
Catalyst: none
Stabilizer: 4-toluenesulfonic acid-methyl ester

Example 5

$R^1$—NH—CO—O—$R^2$: N-phenyl-carbamic acid-isopropylester
Catalyst: none
Stabilizer: none

Example 6

$R^1$—NH—CO—$OR^2$: N-3-tolyl-carbamic acid-ethylester
Catalyst: none
Stabilizer: 4-toluenesulfonic acid-methylester

Example 7

$R^1$—NH—CO—$OR^2$: N-3-tolyl-carbamic acid-isopropylester
Catalyst: none
Stabilizer: none

Example 8

$R^1$—NH—CO—$OR^2$: N-3-(trifluoromethyl)-phenyl-carbamic acid-ethylester
Catalyst: none
Stabilizer: none

Example 9

$R^1$—NH—CO—$OR^2$: N-4-chlorophenyl-carbamic acid-ethylester
Catalyst: none
Stabilizer: none

Example 10

$R^1$—NH—CO—$OR^2$: N-4-chlorophenyl-carbamic acid-ethylester
Catalyst: tin-(II) chloride
Stabilizer: phthalic acid dichloride

Example 11

$R^1$—NH—CO—$OR^2$: N-3,4-dichlorophenyl-carbamic acid-ethyl ester
Catalyst: none
Stabilizer: 4-toluenesulfonic acid-methyl ester

Example 12

$R^1$—NH—CO—$OR^2$: N-3,4-dichlorophenyl-carbamic acid-butyl ester
Catalyst: none
Stabilizer: 4-toluenesulfonic acid chloride

Example 13

$R^1$—NH—CO—$OR^2$: N-3,4-dicylorophenyl-carbamic acid-pentylester
Catalyst: none
Stabilizer: 4-toluenesulfonic acid-methylester

Example 14

$R^1$—NH—CO—$OR^2$: N-isopropyl-carbamic acid-cyclohexyl-ester
Catalyst: none
Stabilizer: none

Example 15

$R^1$—NH—CO—$OR^2$: N-isopropyl-carbamic acid-cyclohexyl-ester
Catalyst: zinc octoate (8 wt. % Zn)
Stabilizer: none

Example 16

$R^1$—NH—CO—$OR^2$: N-isopropyl-carbamic acid-(2-ethyl-hexyl)-ester
Catalyst: none
Stabilizer: none

Example 17

$R^1$—NH—CO—$OR^2$: N-isopropyl-carbamic acid-(2-ethyl-hexyl)-ester
Catalyst: zinc oxide
Stabilizer: 4-toluenesulfonic acid-methyl ester

Examples 18–23

The apparatus used in Examples 18 to 23 is shown schematically in FIG. 2. Reaction vessel A consisted of a 100 liter tank equipped with immersion evaporator and stirrer. The volume of its contents was kept constant at 80 liter. Two nests of cooling pipes arranged inside an apparatus were connected to the tank and used as fractionation columns B and C. Situated between these two condensers was a discharge tray D by means of which the condensate of the fractionation column C was collected, removed and then discharged into a separating distillation column E. The gaseous mixture leaving at the head of the fractionation column C was fed into a second distillation column F serving as separator, optionally after first undergoing an intermediate condensation. A 20 liter tank G equipped with immersion evaporator and stirrer was connected to reaction vessel A to flush out the residue.

When carrying out the process in these examples, the pressure in the fractionation columns and in distillation vessel G was virtually equal to that in reaction vessel A.

Any catalyst and/or stabilizer used was added to the carbamic acid ester introduced into reaction vessel A.

In Examples 18 through 22, the fractions containing isocyanate were removed as condensates from fractionation column C and the pure isocyanates were obtained at the head of column E. In Example 23, the fraction containing isocyanate was removed at the head of fractionation column C and the pure isocyanate was obtained at the head of column F through pipe (208).

Example 18 (see FIG. 2)

10.2 kg/h of molten N-phenyl-carbamic acidethylester were introduced continuously into reaction vessel A through pipe (201). The reaction temperature in reac-

TABLE 1

| Position* | Example | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| (A) | Reaction temp. (°C.) | 190 | 175 | 217 | 200 | 210 | 195 | 220 | 195 | 195 | 205 | 205 | 210 | 240 | 225 | 245 | 220 |
| | Reaction press. (bar) | 0.16 | 0.10 | 0.47 | 0.27 | 0.27 | 0.10 | 0.33 | 0.07 | 0.07 | 0.04 | 0.013 | 0.013 | 1.0 | 1.0 | 1.0 | 1.0 |
| (B) | Oil inlet temp. (°C.) | 148 | 120 | 170 | 155 | 165 | 145 | 131 | 150 | 150 | 142 | 135 | 142 | 176 | 175 | 190 | 188 |
| (C) | Oil inlet temp. (°C.) | 40 | 40 | 68 | 50 | 60 | 35 | 65 | 40 | 40 | 25 | 25 | 70 | 100 | 100 | 130 | 130 |
| (101) | Product feed kg/h | 13.5 | 17.0 | 17.6 | 23.1 | 19.9 | 26.0 | 17.2 | 12.1 | 14.5 | 18.1 | 21.2 | 22.0 | 9.1 | 9.4 | 13.1 | 16.8 |
| | wt. % catalyst | — | 0.1 | — | — | — | — | — | — | 0.05 | — | — | — | — | 0.01 | — | 0.1 |
| | wt. % stabilizer | — | — | 0.1 | — | 0.1 | — | — | — | 0.1 | 0.1 | 0.1 | 0.1 | — | — | — | 0.05 |
| (103) | wt. % $R^1$—NH—CO—$OR^2$ | 98.3 | 96.7 | 98.8 | 98.4 | 96.3 | 98.6 | 98.1 | 95.2 | 93.4 | 96.4 | 97.1 | 99.0 | 93.8 | 94.6 | 97.5 | 96.2 |
| (105) | discharge kg/h | 10.1 | 12.9 | 13.8 | 16.4 | 15.4 | 21.6 | 14.6 | 9.1 | 11.2 | 14.7 | 16.3 | 17.0 | 5.2 | 5.3 | 8.3 | 11.1 |
| | wt. % $R^1$—NCO | 72.0 | 65.7 | 63.1 | 62.8 | 73.8 | 60.8 | 58.4 | 84.0 | 82.8 | 79.8 | 67.5 | 49.7 | — | — | — | — |
| | wt. % $R^2$—OH | — | — | — | — | — | — | — | — | — | — | — | — | 77.5 | 79.4 | 79.1 | 72.5 |
| (106) | discharge (kg/h) | 3.2 | 3.9 | 3.6 | 6.4 | 4.3 | 4.3 | 2.2 | 2.5 | 3.1 | 3.0 | 4.7 | 4.8 | 3.7 | 3.9 | 4.5 | 5.5 |
| | wt. % $R^2$—OH | 90.3 | 85.9 | 95.5 | 83.8 | 93.2 | 95.9 | 95.4 | 97.3 | 91.5 | 98.9 | 94.4 | 84.3 | — | — | — | — |
| | wt. % $R^1$—NCO | — | — | — | — | — | — | — | — | — | — | — | — | 88.1 | 89.6 | 89.4 | 91.7 |
| | Duration of production period (h) | 59 | 14 | 72 | 10 | 45 | 32 | 11 | 58 | 41 | 60 | 8 | 11 | 10 | 12 | 30 | 28 |
| | Selectivity ($R^1$—NCO) (mol-%) | 97 | 98 | 98 | 97 | 98 | 99 | 95 | 94 | 98 | 97 | 98 | 98 | 94 | 96 | 93 | 96 |

*As shown in FIG. 1 tion vessel A was 190° C., the reaction pressure 0.17 bar. The gaseous product mixture leaving reaction vessel A through pipe (202) was partially condensed in fractionation column B which was supplied with oil adjusted to 148° C. The partial condensate returning to reaction vessel A through pipe (203) contained 98.1 wt. % N-phenyl-carbamic acid-ethylester. The gaseous mixture escaping from fractionation column B was partially condensed in fractionation column C which was operated with oil adjusted to 40° C. Condensate containing 72.2 wt. % phenylisocyanate was continuously removed through pipe (204) from the discharge tray D at the rate of 10.1 kg/h. The condensate was introduced into column E where it was fractionally distilled at a pressure of 0.012 bar and a sump temperature of 100° C. 7.2 kg/h of pure phenylisocyanate were obtained at the head of the column from pipe (206) while sump product containing 96.9 wt. % N-phenyl-carbamic acid-ethylester was continuously removed from the column and returned to reaction vessel A through pipe (207). 3.1 kg/h of product mixture containing 90.6% by weight of ethanol were continuously removed from the head of fractionation column C through pipe (205). This mixture was fed into the column, where it was fractionally distilled at a pressure of 1.0 bar and a sump temperature of 100° C. 2.8 kg/h of ethanol were obtained from the head of the column through pipe (208) while sump product containing 90.6 wt. % N-phenyl-carbamic acid-ethylester was continuously removed from the column and returned to reaction vessel A through pipe (209). 1.8 kg/h of liquid product mixture containing 94.4 wt. % N-phenyl-carbamic acid-ethylester were continuously removed from the sump of reaction vessel A and introduced into distillation vessel G where it was distilled at a pressure of 0.17 bar and a sump temperature of 195° C. Evaporating product mixture was returned to reaction vessel A through pipe (211) while residue liquid containing 56.7 wt. % N-phenyl-carbamic acid-ethylester was removed from the sump of the vessel through pipe (212) at the rate of 0.2 kg/h. The selectivity of thermal cleavage for the preparation of phenylisocyanate was found to be 99 mol-%.

Examples 19 to 23 were carried out as in Example 18. The process parameters and results are summarized in Table 2.

Example 19

$R^1$—NH—CO—$OR^2$: N-phenyl-carbamic acid-isopropylester
Catalyst: none
Stabilizer: none

Example 20

$R^1$—NH—CO—$OR^2$: N-3-tolyl-carbamic acid-ethylester
Catalyst: none
Stabilizer: 4-toluenesulfonic acid-methylester

Example 21

$R^1$—NH—(O—$OR^2$: n-3-tolyl-carbamic acid-isopropyl-ester
Catalyst: none
Stabilizer: none

Example 22

$R^1$—NH—CO—$OR^2$: N-(3,4-dichloro-phenyl)-carbamic acid-butylester
Catalyst: none
Stabilizer: 4-toluenesulfonic acid-methylester

Example 23

$R^1$—NH—CO—$OR^2$: N-isopropyl-carbamic acid-(2-ethylhexyl)-ester
Catalyst: di-n-butyl-tin oxide
Stabilizer: 4-toluenesulfonic acid-ethylester

TABLE 2

| Position* | Example | 19 | 20 | 21 | 22 | 23 |
|---|---|---|---|---|---|---|
| (A) | Reaction temp. (°C.) | 200 | 210 | 195 | 205 | 225 |
|  | Reaction press. (bar) | 0.27 | 0.27 | 0.10 | 0.013 | 1.0 |
| (B) | Oil inlet temp. (°C.) | 155 | 165 | 145 | 135 | 190 |
| (C) | Oil inlet temp. (°C.) | 50 | 60 | 35 | 25 | 125 |
| (E) | Sump temp. (°C.) | 145 | 120 | 125 | 140 | 120 |
|  | Pressure (bar) | 0.27 | 0.013 | 0.013 | 0.005 | 0.02 |
| (F) | Sump temp. (°C.) | 110 | 100 | 110 | 100 | 95 |
|  | Pressure (bar) | 1.0 | 1.0 | 1.0 | 1.0 | 1.0 |
| (G) | Sump Temp. (°C.) | 205 | 215 | 200 | 210 | 240 |
|  | Pressure (bar) | 0.27 | 0.27 | 0.10 | 0.013 | 1.0 |
| (201) | Product feed (kg/h) | 15.7 | 15.7 | 19.0 | 15.9 | 13.6 |
|  | wt. % catalyst | — | — | — | — | 0.05 |
|  | wt. % stabilizer | — | 0.1 | — | 0.1 | 0.1 |
| (203) | wt. % $R^1$—NH—CO—$OR^2$ | 98.7 | 95.8 | 97.9 | 98.3 | 96.9 |
| (204) | Product flow (kg/h) | 16.4 | 15.5 | 21.3 | 16.9 | 11.3 |
|  | wt. % $R^1$—NCO | 62.9 | 73.9 | 60.8 | 67.4 | — |
|  | wt. % $R^2$—OH | — | — | — | — | 74.7 |
| (205) | Product flow (kg/h) | 5.9 | 4.4 | 6.1 | 4.6 | 5.7 |
|  | wt. % $R^2$—OH | 87.0 | 91.1 | 96.9 | 95.7 | — |
|  | wt. % $R^1$—NCO | — | — | — | — | 90.4 |
| (206) | Removal of pure product (kg/h) | 10.1 | 11.3 | 12.9 | 11.0 | 8.1 |
| (207) | wt. % $R^1$—NH—CO—$OR^2$ | 96.4 | 95.2 | 99.3 | 93.5 | 89.3 |
| (208) | Removal of pure product (kg/h) | 5.1 | 4.0 | 5.9 | 4.4 | 5.1 |
| (209) | wt. % $R^1$—NH—CO—$OR^2$ | 96.3 | 97.5 | 97.4 | 95.2 | 91.2 |
| (210) | Product flow (kg/h) | 2.9 | 2.6 | 1.9 | 3.9 | 2.0 |
|  | wt. % $R^1$—NH—CO—$OR^2$ | 92.9 | 86.9 | 91.6 | 92.6 | 88.6 |
| (212) | Product flow (kg/h) | 0.4 | 0.4 | 0.2 | 0.4 | 0.4 |
|  | wt. % $R^1$—NH—CO—$OR^2$ | 51.3 | 40.0 | 36.4 | 36.6 | 51.0 |
| Selectivity ($R^1$—NCO) (mol %) | | 97 | 98 | 99 | 97 | 96 |

*As shown in FIG. 2.

Examples 24–25

The use of the condensate obtained in fractionation column C for the preparation of isocyanates $R^3$—NCO is described in Examples 24 and 25. The apparatus illustrated in FIG. 3 was used.

The reaction vessel A was a 100 liter tank equipped with a circulation evaporator. The volume of liquid in this system was kept constant at 90 liters. Two nests of cooling tubes arranged inside an apparatus and connected to this tank were used as fractionation columns B and C. Between these two condensers was situated a discharge tray D in which the condensate of fractionation column C could be collected. The reaction vessels E consisted of three tanks (E, E' and E") arranged in a cascade and equipped with stirrers and immersion evaporators. The volume of liquid was adjusted to 20 liters in each tank. Two 20 liter distillation vessels (G and H), each equipped with a stirrer and immersion evaporator, were used for a stripping distillation of the liquids taken from tank E" and for flushing out the residue. Two separating columns (F and J) were used for fractionating the gaseous product mixtures escaping from the head of the fractionation column C and from the reaction vessels E, E' and E". During the process, the pressure was virtually the same in reaction vessel A, distillation vessel G and fractionation columns B and C.

Example 24 (see FIG. 3)

N-methyl-carbamic acid-ethylester was reacted with fractions containing phenyl isocyanate in the presence of triethylborate as catalyst and chlorobenzene as distillation aid.

Before the reaction was begun, N-phenylcarbamic acid-ethyl ester was introduced into the apparatus and reconverted into phenyl isocyanate by thermal cleavage to the extent necessary for the reaction, and triethylborate and chlorobenzene were introduced into reaction vessels E, E' and E''. Only then was the reaction begun.

The following procedure was carried out after equilibrium had been established:

6.6 kg/h of N-methyl-carbamic acid-ethylester to which 0.05 wt. % triethylborate had been added to compensate for losses were continuously introduced through pipe (306) into reaction vessel E 10.5 kg/h of condensate from fractionation column C containing 72.9 wt. % phenylisocyanate were also continuously introduced into reaction vessel E through pipe (304). The pressure in all three reaction vessels E, E' and E'' was 1.0 bar. The reaction temperature in vessel E was 135° C., in vessel E' 145° C. and in vessel E'' 155° C. Liquid was continuously transferred from vessel E to vessel E' through pipe (313) and liquid from vessel E' to vessel E'' through pipe (315). The gaseous product mixtures escaping from vessels E, E' and E'' through pipes (307, 314 and 316) were combined in pipe (320) to form a mixture containing 42.6 wt. % methylisocyanate, 23.1 wt. % triethylborate, 6.4 wt. % phenylisocyanate and 6.1 wt. % N-methyl-carbamic acid-ethylester as well as some chlorobenzene. This mixture was continuously introduced into column J and fractionally distilled there at a pressure of 1.0 bar and a sump temperature of 110° C. 3.6 kg/h of pure methyl isocyanate were obtained from pipe (321) at the head of the column while 5.0 kg/h of liquid product mixture containing 39.7 wt. % of triethylborate, 11.0 wt. % phenyl isocyanate and 10.5 wt. % N-methyl-carbamic acid-ethylester were continuously removed from the sump of the column through pipe (322) and returned to reaction vessel E. 22.7 kg/h of a liquid enriched with N-phenyl-carbamic acid-ethylester and containing 11.5 wt. % phenylisocyanate, 5.2 wt. % chlorobenzene, 4.9 wt. % triethylborate, 2.7 wt. % N-methyl-carbamic acid-ethyl ester and 0.5 wt. % methylisocyanate were continuously removed from reaction vessel E'' through pipe (317). This liquid was introduced into distillation vessel H where it was subjected to a stripping distillation at a pressure of 0.05 bar and a temperature of 170° C. The gaseous product mixture thereby formed was returned to reaction vessel E through pipe (318) while 13.5 kg/h of a liquid containing 99.4 wt. % N-phenyl-carbamic acid-ethylester were continuously removed from the sump of the vessel through pipe (319) and returned to reaction vessel A. The reaction temperature in reaction vessel A was 190° C. and the reaction pressure 0.17 bar. The gaseous product mixture leaving reaction vessel A through pipe (302) was partially condensed in fractionation column B which was supplied with oil adjusted to 145° C. The condensate returning to reaction vessel A through pipe (303) contained 96.0 wt. % N-phenyl-carbamic acid-ethylester. The gaseous mixture passing through fractionation column B was partially condensed in fractionation column C which was supplied with oil adjusted to 40° C. 3.4 kg/h of gaseous product mixture containing 89.0 wt. % ethanol were removed from the head of fractionation column C through pipe (305). This mixture was introduced into column F where it was fractionally distilled at a pressure of 1.0 bar and a sump temperature of 100° C. 3.0 kg/h of ethanol were continuously obtained from the head of the column through pipe (308) while liquid containing 93.5 wt. % N-phenyl-carbamic acid-ethylester was continuously removed from the sump of the column and returned to reaction vessel A through pipe (309). To flush out the residue, 2.0 kg/h of liquid containing 89.3 wt. % N-phenyl-carbamic acid-ethylester were continuously removed from reaction vessel A through pipe (310) and introduced into distillation vessel G where it was subjected to a stripping distillation at a pressure of 0.17 bar and a temperature of 220° C. The gaseous product mixture which distilled off was returned to reaction vessel A through pipe (311) while 0.3 kg/h of liquid containing 36.7 wt. % N-phenyl-carbamic acid-ethylester were continuously removed from the vessel through pipe (312). To compensate for product losses, 0.3 kg/h of N-phenyl-carbamic acid-ethylester were continuously introduced into reaction vessel A through pipe (301).

The yield of methylisocyanate obtained when the process was carried out continuously was 99% of the theoretical yield, based on the quantity of N-methyl-carbamic acid-ethylester put into the process.

EXAMPLE 25

N-isopropyl-carbamic acid-n-butyl ester ($R^3$—NH—CO—$OR^2$) was reacted with fractions containing cyclohexylisocyanate ($R^1$—NCO) in the presence of tri-n-butylborate as catalyst by the method described in Example 24. The process parameters and results are summarized in Table 3.

TABLE 3

| Position (As indicated in FIG. 3) | |
|---|---|
| (A) | Reaction pressure: 0.39 bar |
| | Reaction temperature: 225° C. |
| (B) | Oil inlet temperature: 175° C. |
| (C) | Oil inlet temperature: 100° C. |
| (E) | Reaction pressure: 0.41 bar |
| | Reaction temperature: 140° C. |
| (E') | Reaction pressure: 0.41 bar |
| | Reaction temperature: 150° C. |
| (E'') | Reaction pressure: 0.41 bar |
| | Reaction temperature: 160° C. |
| (F) | Pressure: 0.39 bar |
| | Temperature in sump: 140° C. |
| (G) | Pressure: 0.39 bar |
| | Temperature: 230° C. |
| (H) | Pressure: 0.03 bar |
| | Temperature: 150° C. |
| (J) | Pressure: 1.0 bar |
| | Temperature in sump: 130° C. |
| (301) | $R^1$—NH—CO—$OR^2$ Input: 0.5 kg/h |
| (303) | 96.3 wt. % $R^1$—NH—CO—$OR^2$ |
| (304) | Product flow: 12.7 kg/h |
| | 69.9 wt. % $R^1$—NCO |
| (305) | 88.6 wt. % $R^2$—OH |
| (306) | Product input: 11.2 kg/h |
| | 0.05 wt. % catalyst |
| (308) | $R^2$—OH discharge: 5.3 kg/h |
| (309) | Product flow: 0.9 kg/h |
| | 78.5 wt. % $R^1$—NH—CO—$OR^2$ |
| (310) | Product flow: 2.9 kg/h |
| | 87.8 wt. % $R^1$—NH—CO—$OR^2$ |
| (312) | Product flow: 0.5 kg/h |
| | 43.4 wt. % $R^1$—NH—CO—$OR^2$ |
| (317) | Product flow: 26.8 kg/h |
| | 10.4 wt. % $R^1$—NCO |
| | 6.9 wt. % catalyst |
| | 0.6 wt. % $R^3$—NH—CO—$OR^2$ |

TABLE 3-continued

| Position (As indicated in FIG. 3) | |
|---|---|
| | 0.2 wt. % $R^3$—NCO |
| (319) | Product flow: 18.0 kg/h |
| | 99.1 wt. % $R^1$—NH—CO—OR$^2$ |
| (320) | 88.1 wt. % $R^3$—NCO |
| | 10.6 wt. % $R^1$NCO |
| (321) | $R^3$—NCO discharge: 5.9 kg/h |
| (322) | Product flow: 0.9 kg/h |
| | 10.4 wt. % $R^3$—NCO |
| | 9.8 wt. % $R^3$—NH—CO—OR$^2$ |
| $R^3$—NCO | Yield: 99% of theoretical yield |

What is claimed is:

1. A continuous process for the thermal cleavage of a carbamic acid ester into an isocyanate of the formula $R^1$—NCO and an alcohol of the formula $R^2$—OH and separation of the thus-produced isocyanate and alcohol, said carbamic acid ester having a boiling point of at least 200° C. and corresponding to the general formula:

$$R^1-NH-CO-OR^2$$

in which
$R^1$ represents an aliphatic hydrocarbon group having a total of 1 to 18 carbon atoms which may be olefinically unsaturated and/or carry inert substituents, a cycloaliphatic hydrocarbon group having a total of 3 to 18 carbon atoms which may be olefinically unsaturated and/or carry inert substituents; an araliphatic hydrocarbon group having 7 to 18 carbon atoms which may carry inert substituents, or an aromatic hydrocarbon group having 6 to 18 carbon atoms which may carry inert substituents; and
$R^2$ represents a group obtained by removal of the hydroxyl group from a primary or secondary aliphatic, cycloaliphatic or araliphatic alcohol having a boiling point which is at least 50° C. above or below the boiling point of the isocyanate corresponding to the formula $R^1$—NCO comprising:
(a) continuously introducing the carbamic acid ester $R^1$—NH—CO—OR$^2$ into a reaction vessel;
(b) boiling the carbamic acid ester for a period such that the average dwell time is from 1 to 20 hours at a temperature of from 160° to 260° C. and a pressure of from 0.001 to 2 bar to partially cleave the carbamic acid ester into isocyanate and alcohol;
(c) partially condensing the vapor product of (b) in a first fractionation column to form (i) a condensate containing carbamic acid ester and (ii) a gaseous mixture;
(d) returning the condensate (i) to the reaction vessel; and
(e) partially condensing the gaseous mixture (ii) in a second fractionation column to form a condensate made up of residual carbamic acid ester and the higher boiling of the isocyanate and alcohol fractions.

2. The process of claim 1 wherein $R^2$ represents a group obtained by removal of the hydroxyl group from an alcohol having a boiling point which is at least 50° C. higher than the boiling point of $R^1$—NCO so that the isocyanate fraction is obtained in gaseous form from the second fractionation column.

3. The process of claim 2 wherein the isocyanate fraction recovered is further separated to yield pure isocyanate and a distillation residue consisting essentially of carbamic acid ester.

4. The process of claim 3 wherein the carbamic acid ester residue is returned to the reaction vessel.

5. The process of claim 2 wherein the condensate recovered from the second fractionation column is separated by distillation into a distillate consisting essentially of the alcohol $R^2$—OH and a distillation residue consisting essentially of carbamic acid ester.

6. The process of claim 5 wherein the carbamic acid ester residue is returned to the reaction vessel.

7. The process of claim 1 wherein $R^2$ represents a group obtained by removal of the hydroxyl group from an alcohol having a boiling point which is at least 50° C. below the boiling point of $R^1$—NCO so that the alcohol fraction is obtained in gaseous form from the second fractionation column.

8. The process of claim 7 wherein the condensate produced in the second fractionation column is separated by distillation into pure isocyanate and a distillation residue consisting essentially of carbamic acid ester.

9. The process of claim 8 wherein the distillation residue is returned to the reaction vessel.

10. The process of claim 7 wherein the gaseous product of the second fractionation column is separated by distillation into pure alcohol and a distillation residue consisting essentially of carbamic acid ester.

11. The process of claim 10 wherein the distillation residue is returned to the reaction vessel.

12. The process of claim 1 wherein the reaction mixture in the reactor vessel further comprises a Lewis acid catalyst.

13. The process of claim 1 wherein the reaction mixture in the reactor vessel further comprises a stabilizer selected from the group consisting of carboxylic acid chlorides, sulfonic acid chlorides, sulfonic acid esters, alkylating compounds and mixtures thereof.

14. A process for the production of a monoisocyanate of the formula $$R^3-NCO$$

which has a boiling point at least 50° C. below the boiling point of the isocyanate $R^1$—NCO wherein
$R^1$ and $R^3$ each may represent an aliphatic hydrocarbon group having a total of 1 to 18 carbon atoms which may be olefinically unsaturated and/or carry inert substituents, a cycloaliphatic hydrocarbon group having a total of 3 to 18 carbon atoms which may be olefinically unsaturated and/or carry inert substituents, an araliphatic hydrocarbon group having 7 to 18 carbon atoms which may carry inert substituents, or an aromatic hydrocarbon group having 6 to 18 carbon atoms which may carry inert substituents provided that the required difference in boiling point is met comprising:
(a) continuously reacting (i) a carbamic acid ester corresponding to the formula $$R^3-NH-CO-OR^2$$

wherein
$R^2$ represents a group such as is obtained by removal of the hydroxyl group from a primary or secondary aliphatic, cycloaliphatic or araliphatic alcohol whose boiling point is at least 50° C. above or below the boiling point of the isocyanate corresponding to the general formula R$^1$—NCO and R$^1$ and R$^3$ are as defined above with (ii) a condensate containing an isocyanate corresponding to the general formula R$^1$—NCO and a carbamic acid ester corresponding to the formula R$^1$—NH—CO—OR$^2$ in an amount such that the molar ratio of carbamic acid ester R$^3$—NH—CO—OR$^2$ to isocyanate R$^1$—NCO is within the range from 1:1 to 1:10 at a temperature of from 50° to 200° C. and a pressure such that the reaction mixture boils to effect transurethanation;

(b) collecting the gaseous product mixture formed in (a); and (c) separating the isocyanate R$^3$—NCO from the mixture of (b).

15. The process of claim 14 wherein the isocyanate R$^3$—NCO is separated from the mixture of (b) by distillation.

16. The process of claim 14 wherein any residue from the separation of step (c) is returned to the reaction vessel.

17. The process of claim 14 wherein a liquid product mixture enriched with carbamic acid ester of the formula R$^1$—NH—CO—OR$^2$ is continuously removed from the reaction vessel and fed to a second reaction vessel in which the carbamic acid ester is cleaved to form R$^1$—NCO and R$^2$—OH fractions.

18. The process of claim 17 wherein any carbamic acid ester of the formula R$^3$—NH—CO—OR$^2$ present in the enriched liquid product mixture is removed before that mixture is fed to the second reactor.

19. The process of claim 17 wherein any isocyanate of the formula R$^1$—NCO is removed from the enriched liquid product mixture by distillation prior to feeding that mixture to the second reactor.

20. The process of claim 19 wherein the isocyanate R$^1$—NCO removed from the mixture is reused as a reactant in the preparation of a monoisocyanate of the formula R$^3$—NCO.

21. The process of claim 14 wherein the reaction mixture further comprises a Lewis acid catalyst.

22. The process of claim 21 wherein the Lewis acid is a boric acid trialkylester.

23. The process of claim 22 wherein the boric acid trialkylester corresponds to the formula $$B(OR^2)_3.$$

* * * * *